(12) United States Patent
Pant et al.

(10) Patent No.: US 9,842,241 B2
(45) Date of Patent: Dec. 12, 2017

(54) BIOMETRIC CRYPTOGRAPHY USING MICROMACHINED ULTRASOUND TRANSDUCERS

(71) Applicant: Intel Corporation, Santa Clara, CA (US)

(72) Inventors: Mondira D. Pant, Westborough, MA (US); Mohamed A. Abdelmoneum, Portland, OR (US); Tanay Karnik, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 116 days.

(21) Appl. No.: 14/975,949

(22) Filed: Dec. 21, 2015

(65) Prior Publication Data
US 2017/0177917 A1    Jun. 22, 2017

(51) Int. Cl.
*G06K 9/00*     (2006.01)
*H04L 9/32*     (2006.01)
*G01N 29/24*    (2006.01)

(52) U.S. Cl.
CPC ....... *G06K 9/0002* (2013.01); *G01N 29/2406* (2013.01); *G06K 9/00087* (2013.01);
(Continued)

(58) Field of Classification Search
CPC ......... H01L 2924/0002; H01L 2924/00; H01L 21/76852; H01L 21/76879;
(Continued)

(56) References Cited

U.S. PATENT DOCUMENTS 7,839,722 B2 * 11/2010 Wagner ................. B06B 1/0292
                                                    367/181
8,821,009 B2    9/2014 Abdelmoneum
(Continued)

OTHER PUBLICATIONS

International Searching Authority, "Notification of Transmittal of the International Search Report and the Written Opinion of the International Searching Authority," dated Feb. 14, 2017, in International application No. PCT/US2016/062387.
(Continued)

*Primary Examiner* — Kim Vu
*Assistant Examiner* — Michael Vanchy, Jr.
(74) *Attorney, Agent, or Firm* — Trop, Pruner & Hu, P.C.

(57) ABSTRACT

An embodiment includes an ultrasonic sensor system comprising: a backend material stack including a first metal layer between a substrate and a second metal layer with each of the first and second metal layers including a dielectric material; a ultrasonic sensor including a chamber, having a negative air pressure, that is sealed by first and second electrodes coupled to each other with first and second sidewalls; an interconnect, not included in the sensor, in the second metal layer; wherein (a) a first vertical axis intersects the substrate, the chamber, and the first and second electrodes, (b) a second vertical axis intersects the interconnect and the substrate, (c) a first horizontal axis intersects the chamber, the interconnect, and the first and second sidewalls, and (d) the first and second electrodes and the first and second sidewalls each include copper and each are included in the second metal layer.

25 Claims, 11 Drawing Sheets

(52) U.S. Cl.
CPC ..... *G06K 9/00885* (2013.01); *G06K 9/00892* (2013.01); *H04L 9/3231* (2013.01); *G06K 2009/00932* (2013.01)

(58) Field of Classification Search
CPC ............. H01L 21/76885; H01L 23/522; H01L 23/5226; H01L 23/5283; H01L 23/5286; H01L 23/5329; H01L 41/0926; B06B 1/0292; B06B 1/06; B06B 1/0622; B06B 1/0688; Y10T 29/49005; Y10T 29/49155; Y10T 29/42; Y10T 29/49007; Y10T 29/4908; Y10T 29/49128; B81B 2201/0214; B81B 2201/0285; B81B 2203/04; B81B 3/0021; G06K 9/0002; H03H 3/02; H03H 3/08; H03H 9/02622; H03H 9/172; Y10S 310/80
See application file for complete search history.

(56) References Cited

U.S. PATENT DOCUMENTS

| | | | |
|---|---|---|---|
| 2006/0116585 A1* | 6/2006 | Nguyen-Dinh | B06B 1/0292 600/459 |
| 2008/0066279 A1 | 3/2008 | Chen et al. | |
| 2008/0184549 A1 | 8/2008 | Nguyen-Dinh et al. | |
| 2009/0122651 A1 | 5/2009 | Kupnik et al. | |
| 2013/0208572 A1 | 8/2013 | Klee et al. | |
| 2014/0355381 A1 | 12/2014 | Lal et al. | |
| 2015/0179562 A1 | 6/2015 | Fischer | |

OTHER PUBLICATIONS

Oralkan, Omer, et al., "Capacitive Micromachined Ultrasonic Transducers: Next-Generation Arrays for Acoustic Imaging?" IEEE Transactions on Ultrasonics, Ferroelectrics, and Frequency Control, vol. 49, No. 11, Nov. 2002, 15 Pages.

Ergun, A.S., et al., "Capacitive Micromachined Ultrasonic Transducer Technology for Medical Ultrasound Imaging," Medical Imaging 2005: Ultrasonic Imaging and Signal Processing, Proc. of SPIE vol. 5750, pp. 58-68.

Soutar, Colin, et al., "Biometric Encryption™," Bioscrypt Inc.,, Chapter 22 in ICSA Guide to Cryptography, McGraw-Hill (1999), 28 Pages.

Khuri-Yakub Ultrasonic Group, "General Description and Advantages of CMUTs," http://www-kyg.stanford.edu/khuriyakub/opencms/en/research/cmuts/general/index.html, accessed Dec. 3, 2015, 2 Pages.

Jambandhu, P.K., et al., "Novel biometric digital signatures for Internet-based applications," Journal of Information Management & Computer Security, 2001, pp. 205-212.

Tiwari, S.P., et al., "Pentacene Organic Field Effect Transistors on Flexible substrates with polymer dielectrics," IEEE, 2007, 2 Pages.

Tetzner, Kornelius, et al., "Organic Field-Effect Transistors Based on a Liquid-Crystalline Polymeric Semiconductor using SU-8 Gate Dielectrics on Flexible Substrates," Materials 2014, 7, 7226-7242.

\* cited by examiner

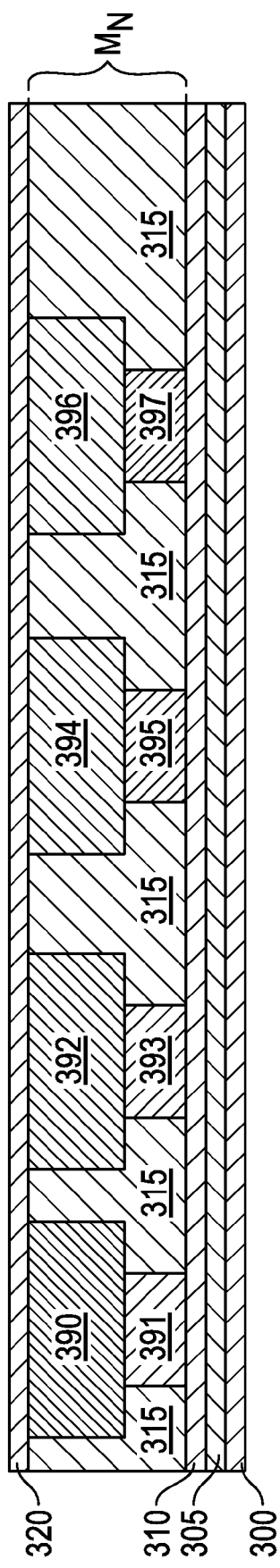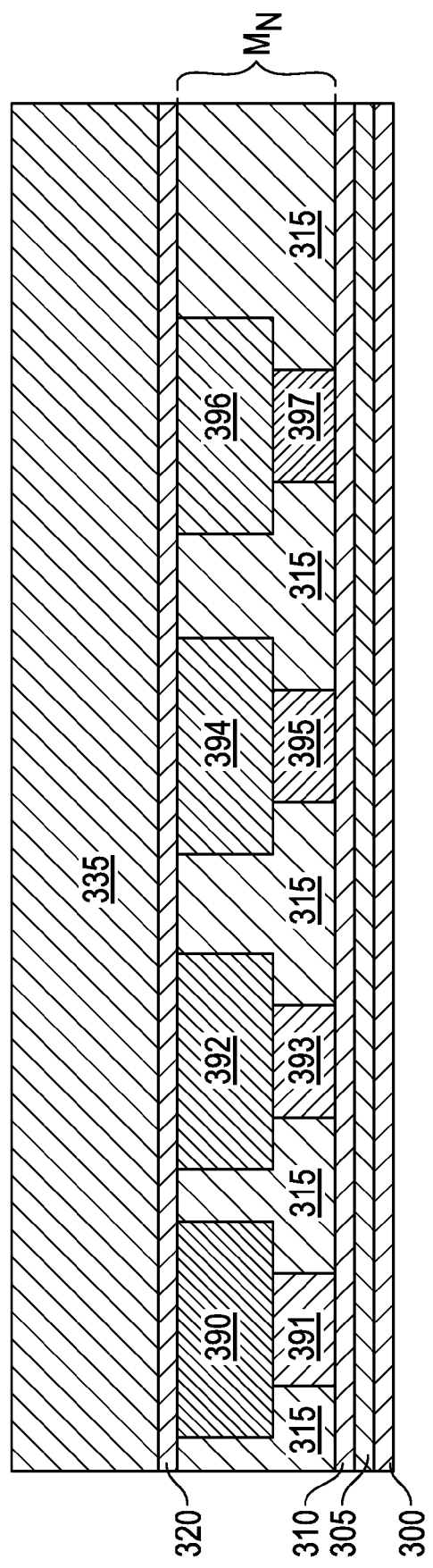

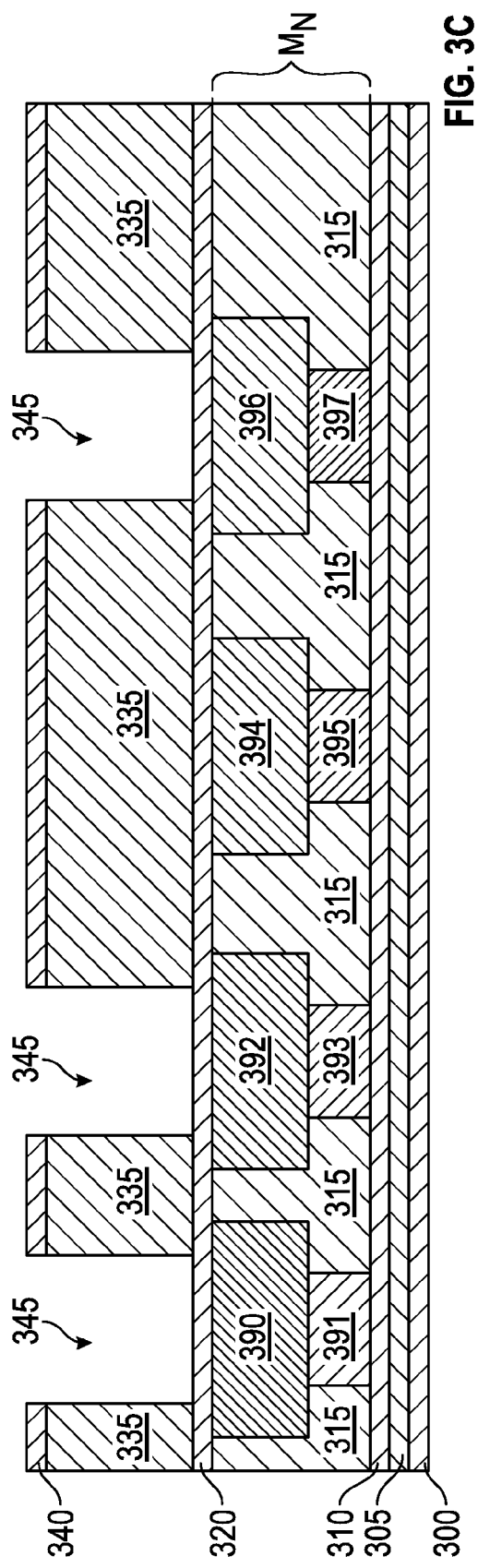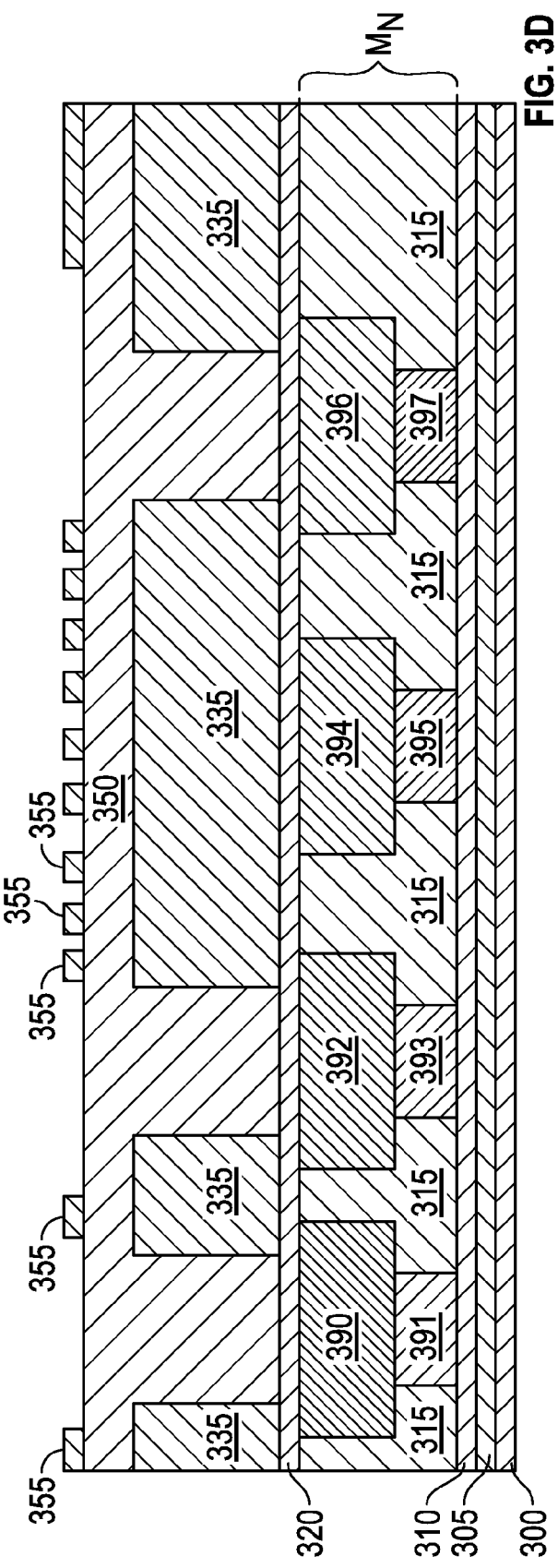

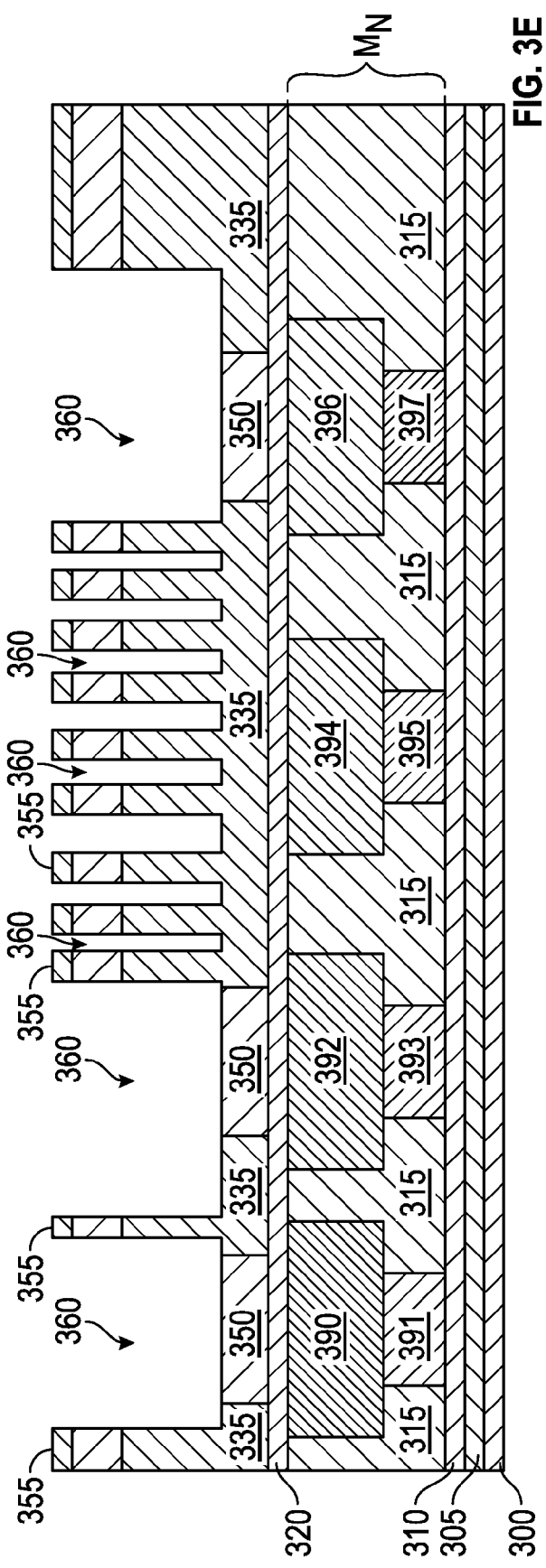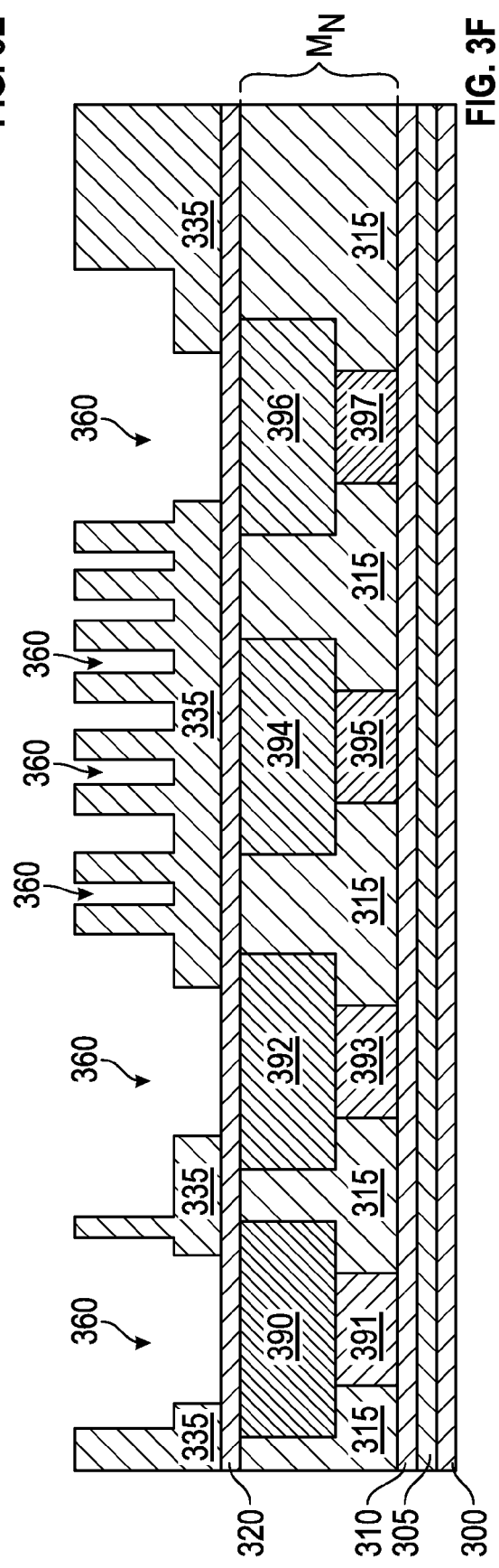

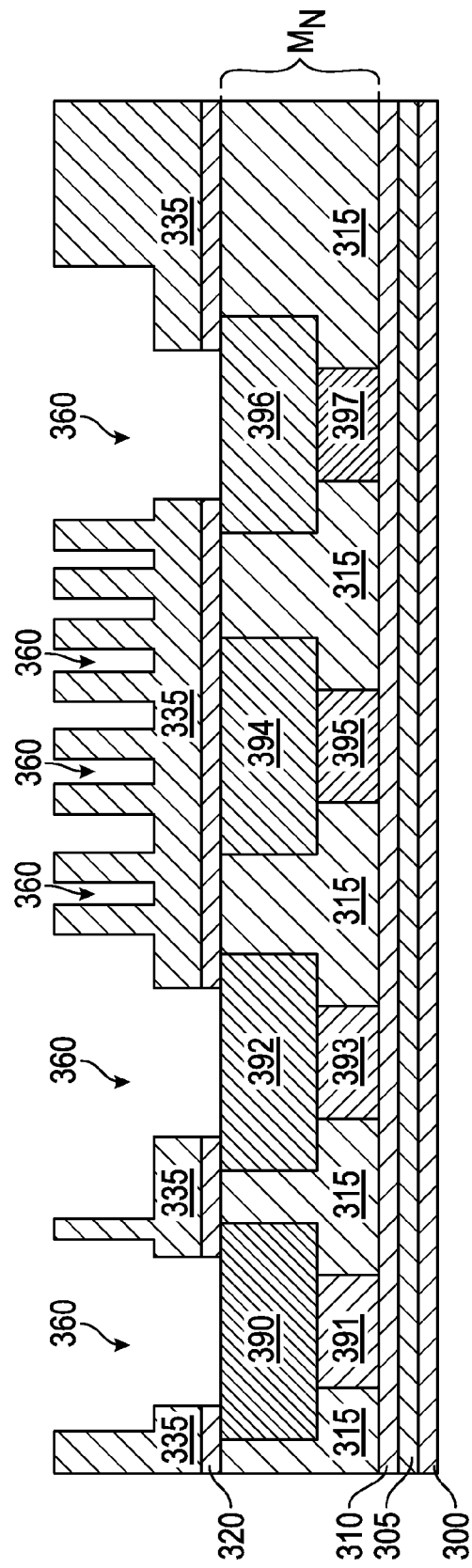
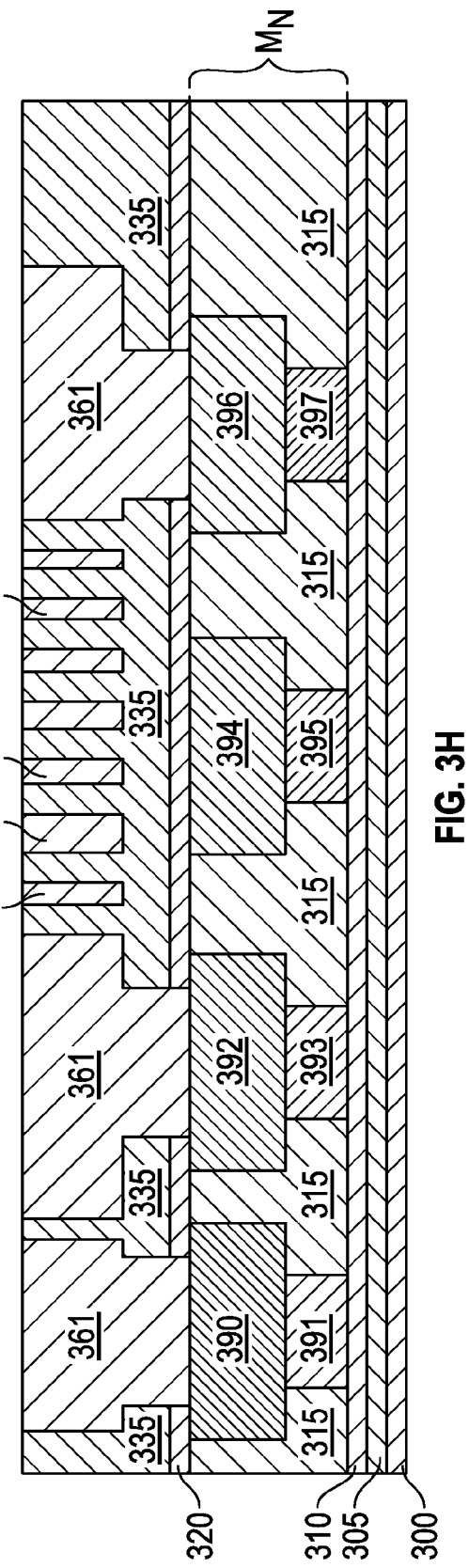
FIG. 3G
FIG. 3H

BIOMETRIC CRYPTOGRAPHY USING MICROMACHINED ULTRASOUND TRANSDUCERS

TECHNICAL FIELD

Embodiments of the invention are in the field of cryptography.

BACKGROUND

With the proliferation of information exchange across the Internet and the storage of sensitive data on open networks, cryptography has become an important feature of computer security. In many cases data is secured using a symmetric cipher system. Public-key systems are used for digital signatures and for secure symmetric key exchange between users. However, regardless of whether a user deploys a symmetric and/or a public-key system, the security is dependent on the secrecy of the secret or private key, respectively. Because of the large size of a cryptographically-strong key, it is not feasible to require a user to remember and enter the key each time it is required. Instead, the user is typically required to choose an easily remembered passcode that is used to encrypt the cryptographic key. To retrieve the cryptographic key, the user is prompted to enter the passcode, which will then be used to decrypt the key.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 3(a)-(j) depict a manufacturing process in an embodiment.

DETAILED DESCRIPTION

Figure 1:
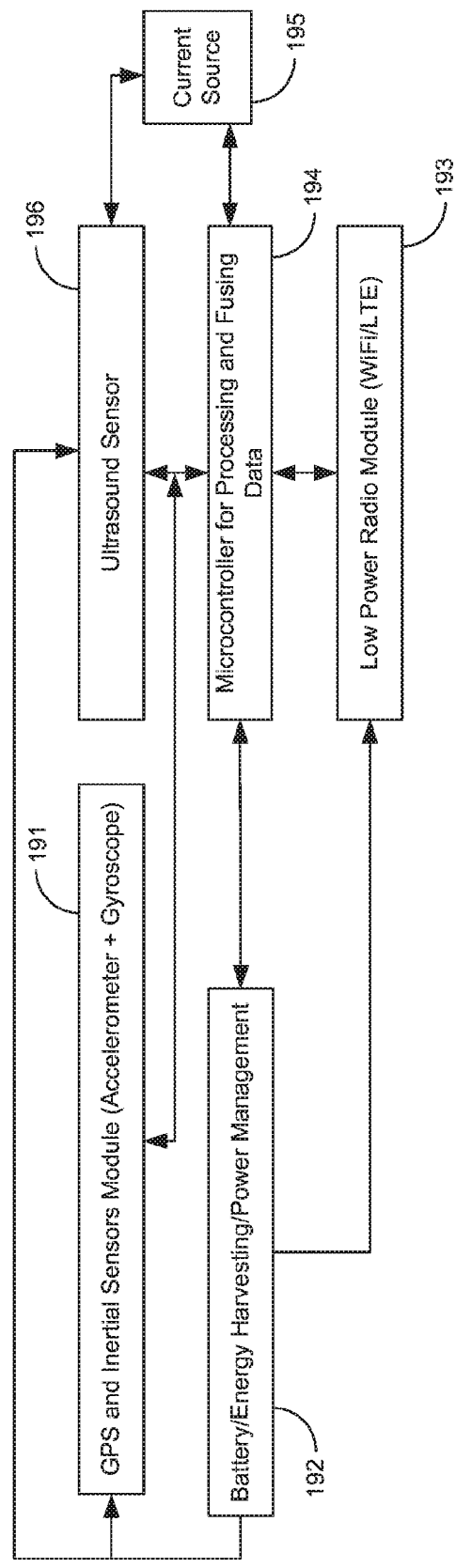
FIG. 1 includes a cryptography system in an embodiment.

Reference will now be made to the drawings wherein like structures may be provided with like suffix reference designations. In order to show the structures of various embodiments more clearly, the drawings included herein are diagrammatic representations of semiconductor/circuit structures. Thus, the actual appearance of the fabricated integrated circuit structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. For example, not every layer of a semiconductor device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Applicant determined there are two main problems with the above method of passcode-based security. First, the security of the cryptographic key, and hence the cipher system, is now only as good as the passcode. Due to practical problems of remembering various passcodes, some users tend to choose simple words, phrases, or easily remembered personal data, while others resort to writing the passcode down on an accessible document to avoid data loss. Obviously these methods pose potential security risks. The second problem concerns the lack of direct connection between the passcode and the user. Because a passcode is not tied to a user, the system running the cryptographic algorithm is unable to differentiate between the legitimate user and an attacker who fraudulently acquires the passcode of a legitimate user.

As an alternative to passcode protection, biometric authentication offers a new mechanism for key security by using a biometric to secure the cryptographic key. A biometric is defined as a unique, measurable, biological characteristic or trait for recognizing or verifying the identity of an animal (e.g., human being, dog). Instead of entering a passcode to access the cryptographic key, the use of this key is guarded by biometric authentication. When a user wishes to access a secured key, he or she will be prompted to allow for the capture of a biometric sample. If this verification sample matches the enrollment template, then the key is released and can be used to encrypt or decrypt the desired data. Thus, biometric authentication can replace the use of passcodes to secure a key. This offers both convenience, as the user no longer has to remember a passcode, and secure identity confirmation, since only the valid user can release the key.

Applicant analyzed various conventional methods that can be deployed to secure a key with a biometric.

Applicant determined a first method involves remote template matching and key storage. The biometric image is captured and the corresponding template is sent to a secure location for template comparison. If the user is verified, then the key is released from the secure location. This provides a convenient mechanism for the user, as they no longer need to remember a passcode. This method may work well in a physical access application where the templates and keys may be stored in a secure location physically separated from the image capture device. In this scenario, the communication line must also be secured to avoid eavesdropper attacks. However, for personal computer use, the keys would likely be stored in the clear on a user's hard drive, which is not secure.

Applicant determined a second method involves hiding the cryptographic key within the enrollment template itself via a trusted (secret) bit-replacement algorithm. Upon successful authentication by the user, this trusted algorithm simply extracts the key bits from the appropriate locations and releases the key into the system. Unfortunately, this implies that the cryptographic key will be retrieved from the same location in a template each time a different user is authenticated by the system. Thus, if an attacker could determine the bit locations that specify the key, then the attacker could reconstruct the embedded key from any of the other users' templates. If an attacker had access to the enrollment program then he could determine the locations of the key by, for example, enrolling several people in the system using identical keys for each enrollment. The attacker then needs only to locate those bit locations with common information across the templates.

Applicant determined a third method is to use data derived directly from a biometric image. Data derived from the biometric (in essence, the biometric template) is used directly as a cryptographic key. However, there are two main problems with this method. First, as a result of changes in the biometric image due to environmental and physiological factors, the biometric template is generally not consistent enough to use as a cryptographic key. Secondly, if the cryptographic key is ever compromised, then the use of that particular biometric is irrevocably lost. In a system where periodic updating of the cryptographic key is required, this is problematic.

Applicant determined a fourth method for securing a key using a biometric. The method does not use an independent, two-stage process to first authenticate the user and then release the key. Instead, the key is linked with the biometric at a more fundamental level during enrollment, and is later retrieved using the biometric during verification. Furthermore, the key is completely independent of the biometric data, which means that, firstly, the use of the biometric is not forfeited if the key is ever compromised, and secondly, the key can be easily modified or updated at a later date. During enrollment, the process combines the biometric image with a digital key to create a secure block of data. The digital key can be used as a cryptographic key. The secure block of data is secure in that neither the fingerprint nor the key can be independently obtained from it. During verification, the algorithm retrieves the cryptographic key by combining the biometric image with the secure block of data. Thus, the method does not simply provide a yes/no response in user authentication to facilitate release of a key, but instead retrieves a key that can only be recreated by combining the biometric image with the secure block of data. The process provides a secure method for key management to complement existing cipher systems.

In contrast, an embodiment applies a low-cost based ultrasound imaging technology that fits into small form factors like a Smartphone or even smaller wearable devices (e.g., nodes on the Internet of Things (IoT)) to generate on-the-fly images for biometric encryption. Embodiments have unique capabilities including fitting into extremely small form factors, extremely reliable authentication (even if the finger is moist), extremely low power, and low cost.

FIG. 1 shows a system-on-chip (SoC) 190 with the following modules: module 101 (global positioning system (GPS) and Inertial Sensors Module), module 192 (battery/energy harvesting and power management), module 193 (low power radio module), module 194 (microcontroller), module 195 (current source), and module 196 (ultrasonic sensor).

A module as used herein refers to any hardware, software, firmware, or a combination thereof. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices. However, in another embodiment, logic also includes software or code integrated with hardware, such as firmware or micro-code.

Returning to FIG. 1, module 191 may be used to detect motion and position. Module 192 may be used for powering SoC 190. Module 193 may be used for communications with nodes beyond SoC 190. Controller module 194 (sometimes referred to as logic module) may control current application from current source 195 to sensor 196. Module 194 may reconstruct biometric identification from biometric sensor 196. Sensor 196 may be a capacitive ultrasonic sensor (e.g., micro machine ultrasound transducer (CMUT)). Sensor 196 may be on a flexible substrate that is conformal to a user's skin. This may promote transmission of ultrasonic energy to and from a user, such as a user's finger. The conformal flexible substrate may be imbedded into a platform surface (e.g., gun handle or computing node touch pad). Ultrasound may be used to perform tissue (e.g., finger) scan identification where it shows better quality and identification accuracy than optical finger identification technologies.

Flexible/polymer substrates require use of low temperature deposition materials like metals. An embodiment accounts for this using a copper (Cu) and silicon carbide based sensor that can be formed using the low temperatures for the flexible polymer base of the SoC. By implementing the transducer/sensor on the flexible substrate an embodiment accomplishes the need for a conformal sensing surface at a low cost. The interconnects of the flexible substrate connect the transducer array (e.g., an array include sensors such as that of FIG. 3(*j*)) to readout electronics implemented on standard CMOS technology chip along with the logic/GPS/RF shown in FIG. 1. Prior resonator technologies could not be so readily integrated with CMOS processes. MUT (Micromachined Ultrasound Transducer) embodiments enable the best of ultrasound at a chip scale—quality imaging with a small form factor and low power consumption all at a low price using manufacturing methods that are already readily available. Previous ultrasound based imaging solutions have been bulky, expensive, non-CMOS compatible, and slow making their use in small form factor applications prohibitive.

Attention now turns towards the manufacture of an embodiment of the sensor.

Once semiconductor wafers are prepared, a large number of process steps are still necessary to produce desired semiconductor integrated circuits. In general the steps can be grouped into four areas: Front End Processing, Back End Processing, Test, and Packaging.

Front End Processing refers to the initial steps in the fabrication. In this stage the actual semiconductor devices (e.g., transistors) are created. A typical front end process includes: preparation of the wafer surface, patterning and subsequent implantation of dopants to obtain desired electrical properties, growth or deposition of a gate dielectric, and growth or deposition of insulating materials to isolate neighboring devices.

Once the semiconductor devices have been created they must be interconnected to form the desired electrical circuits. This "Back End Processing" involves depositing various layers of metal and insulating material in the desired pattern. Typically the metal layers consist of aluminum, copper, and the like. The insulating material may include $SiO_2$, low-K materials, and the like. The various metal layers are interconnected by interconnects, which may include a line portion and a via portion. Vias may be formed by etching holes in the insulating material and depositing metal (e.g., Tungsten) in them. The line portion may be formed by etching trenches in the insulating material and depositing metal in them.

Once the Back End Processing has been completed, the semiconductor devices are subjected to a variety of electrical tests to determine if they function properly. Finally, the wafer is cut into individual die, which are then packaged in packages (e.g., ceramic or plastic packages) with pins or other connectors to other circuits, power sources, and the like.

Figure 2:
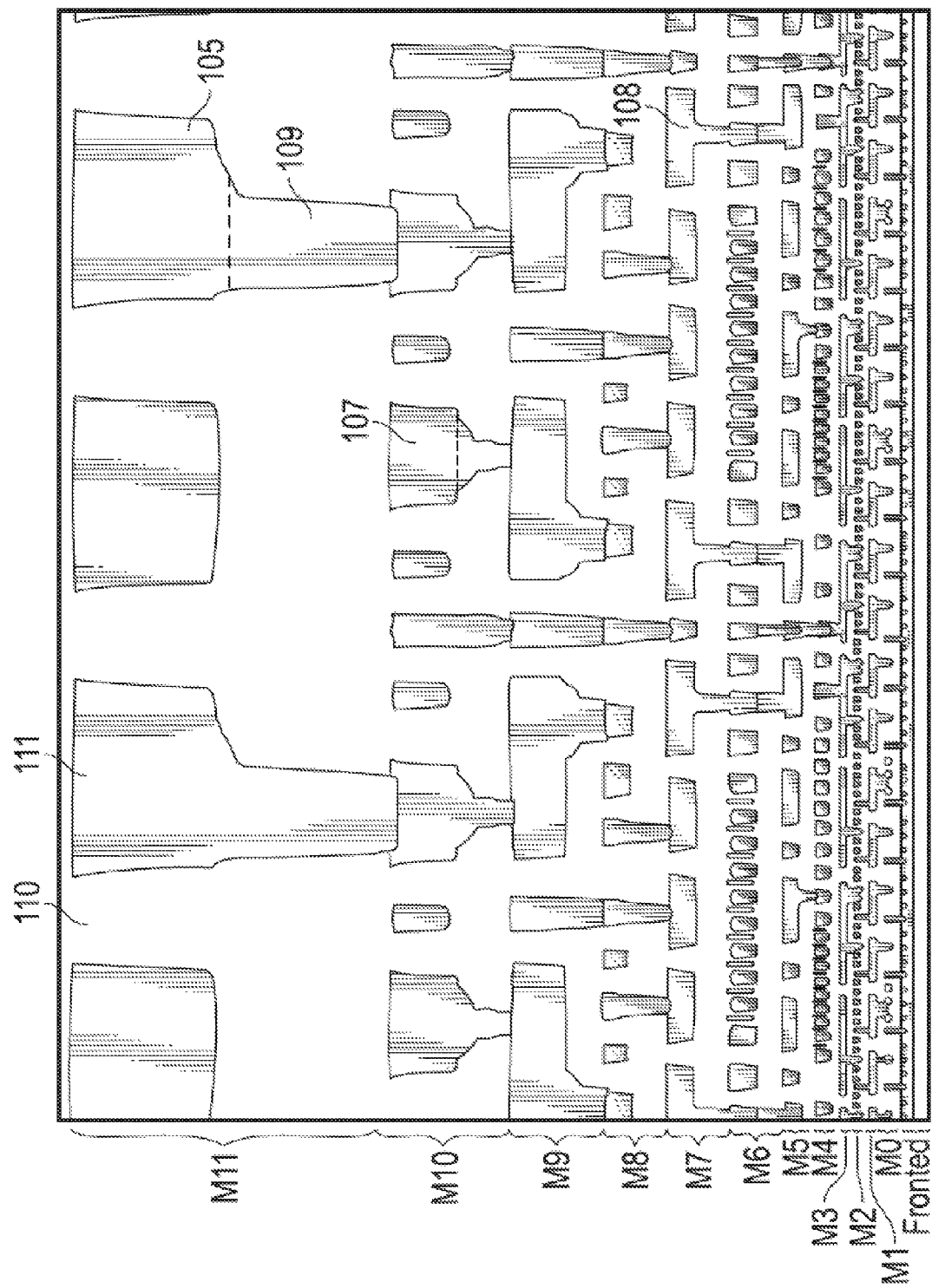
FIG. 2 includes a material stack, having an ultrasound sensor located in a backend metal layer, in an embodiment.

FIG. 2 depicts a multi-metal layer embodiment. A frontend portion includes a device layer on a substrate. The device layer may include transistors and the like. A backend portion includes 12 metal layers (M0, M1, M2, M3, M4, M5, M6, M7, M8, M9, M10, and M11). This is just an example and other embodiments may include more (e.g., 14, 16, 18, 20 or more) or less (e.g., 4, 6, 8) metal layers. The particular embodiment of FIG. 2 includes a bottom metal layer (M0), a top metal layer (M11), and a plurality of metal layers (M1, M2, M3, M4, M5, M6, M7, M8, M9, and/or M10) between the bottom and top metal layers. The "bottom metal layer" is so named because the backend portion includes no metal layer between the bottom metal layer and a top of the frontend portion. The "top metal layer" is so named because the backend portion includes no metal layer between the top metal layer and the top of the backend portion. FIG. 2 discloses various trenches 111, 105, 107, 108 and vias 109. The interconnects are within dielectric 110. The metal layers may have varying thicknesses.

In an embodiment, the metal patterning of M11 (or other metal layers) may be performed with a "dual-Damascene" process whereby the underlying silicon oxide insulating layer is patterned with open trenches where the conductor should be. A thick coating of copper that significantly overfills the trenches is deposited on the insulator, and chemical-mechanical planarization (CMP) is used to remove the copper (known as overburden) that extends above the top of the insulating layer. Copper sunken within the trenches of the insulating layer is not removed and becomes the patterned conductor (e.g., interconnect). Dual-Damascene processes generally form and fill two features with copper at once (e.g., trench 105 overlying via 109 may both be filled with a single copper deposition using dual-Damascene processing).

In an embodiment, the backend portion is coupled to a plurality of contact bumps (not shown in FIG. 2), such as Controlled Collapse Chip Connection ('C4') bumps.

As mentioned above, M11 is the top metal layer in the example of FIG. 2. However, that is not implying that M11 is the top layer in general or that there is no metal above M11. Instead, M11 is a "top metal layer" in that it is topmost of not all layers or any layer with metal but of the "metal layers" as those of ordinary skill in the art would construe that term. In other words, once the semiconductor devices have been created, they must be interconnected to form the electrical circuits. This occurs in a series of wafer processing steps collectively referred to as Back-end-of-line (BEOL) (not to be confused with back end of chip fabrication, which refers to the packaging and testing stages). BEOL processing involves creating metal interconnecting wires that are isolated by dielectric layers. These backend layers including metal interconnecting wires that are isolated by dielectric material are "metal layers". In other words, the "top metal layer" in the context addressed herein is a top interconnect metal layer that includes dielectric material. The top metal layer may include a top damascene formed interconnect layer that includes dielectric material. This top metal layer is formed using an interconnect formation process performed in a semiconductor fabrication (FAB) facility. Layers above this "top metal layer" are classified as part of BEOL wiring layers (e.g., typified by layers supported at outsourced assembly and test (OSAT) houses, not FABs).

FIGS. 3(a)-(j) depict various stages of manufacture for the ultrasonic sensor.

FIG. 3(a) illustrates an early stage of material for manufacturing an ultrasonic sensor. Silicon carrier wafer 300 carries photoresist 305 upon which polymer layer 310 has been deposited. In one embodiment, polymer layer 310 is a spin on resist polymer or a pyraline. Inter-Layer Dielectric (ILD) 315, input electrode 394 and output electrodes 392, 396 are formed on polymer 310. The output electrodes may include trench 392, 396 and vias 393, 397 and the input electrode may include trench 394 and via 395. Etch stop 320 is applied. Trench 390 and via 391 are interconnects that may couple to other portions of the SoC that includes the ultrasonic sensor. Level Mn denotes this metal level may be situated at any of various metal levels, such as any of M0-M11 of FIG. 2.

FIG. 3(b) illustrates another layer of ILD 335 on etch stop 620. FIG. 3(c) illustrates ILD 335 after deposition of photoresist 340 and etching of vias 345 in ILD 35. FIG. 3(d) illustrates deposition of a sacrificial light-absorbing material (SLAM) layer 350 and photoresist 355. FIG. 3(e) illustrates a trench 360 that has been etched defined by photoresist 355. FIG. 3(f) illustrates the structure after photoresist 355 and SLAM 350 have been stripped.

Figure 3I:
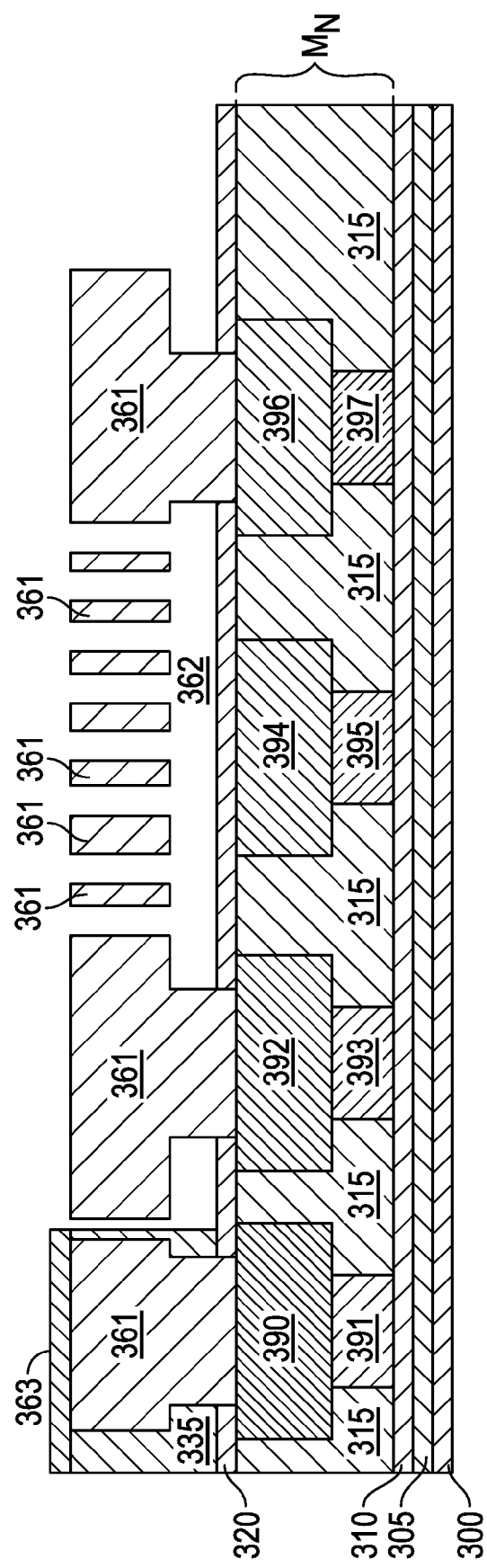
Figure 3J:
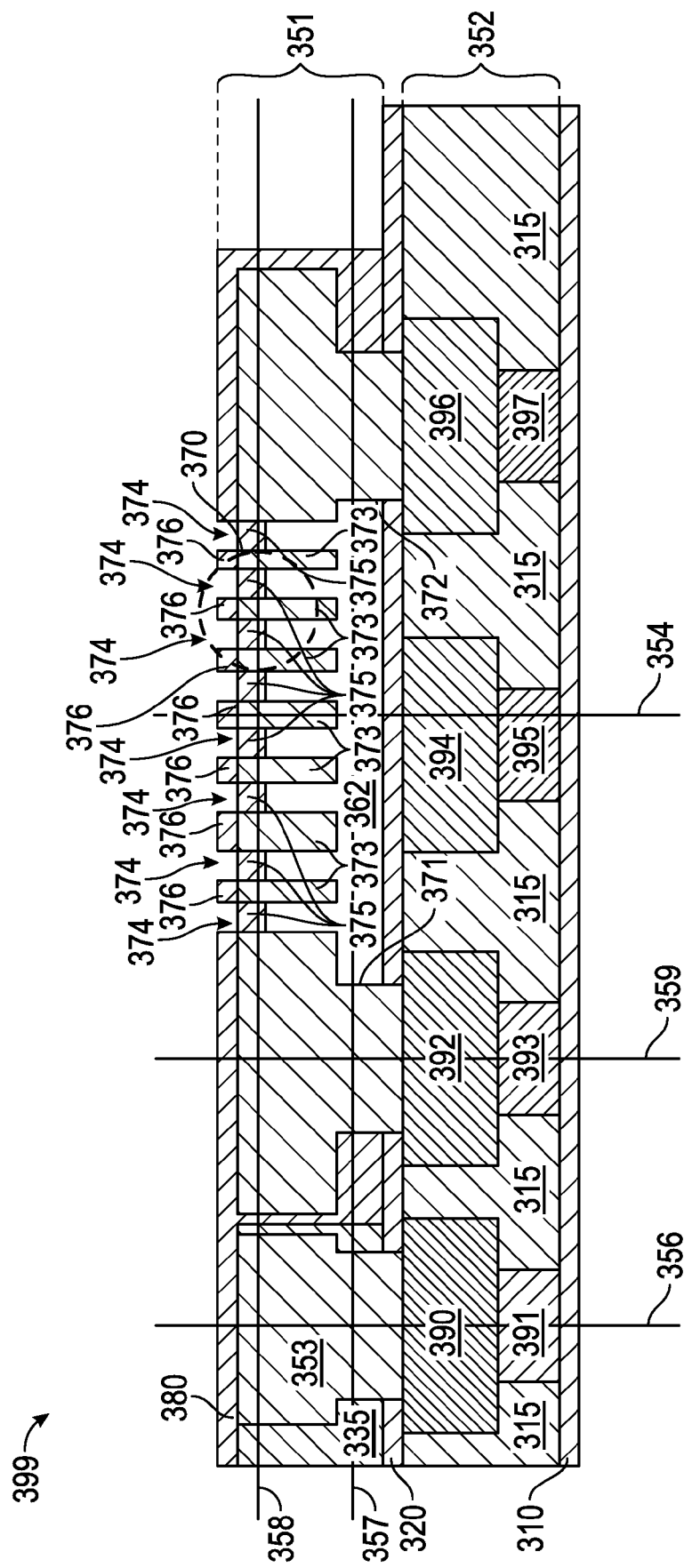

FIG. 3(g) illustrates the structure after etch stop (silicon carbide) 320 has been etched. FIG. 3(h) illustrates the structure after electroplating of copper 361 and polishing. FIG. 3(i) illustrates etching of ILD 335 to yield chamber 362. FIG. 3(j) illustrates deposition of silicon carbide 380 to seal the etch/release holes and create vacuum packed cavity 362. Furthermore, the carrier wafer 300 and photoresist 305 have been stripped. The resulting structure is then on a flexible substrate 310 as described above.

The sensor of FIG. 3(j) has a silicon carbide/copper stack that is both flexible enough (due to copper) to allow upper portion 370 to flex in response to reflected ultrasonic energy yet stiff enough (due to silicon carbide) to not sag or loose resiliency. Thus, sensor 399 includes copper side walls 371, 372, perforated copper membrane 373, where the perforations 374 are sealed by silicon carbide 375. The silicon carbide film is deposited when the device is in a vacuum chamber (air in the cavity 362 is pumped out during fabrication). Silicon carbide layer 376 on top of the copper membrane 373 provides additional stiffness so the copper does not sag and provides geometrical thermal compensation so the resonance frequency does not drift too much when temperature changes. Further, the relatively dense copper (as compared to aluminum) has more relatively greater mass (as compared to aluminum) which provides better sensitivity.

The frequency of the upper electrode may be described as:

$$f_{0=\frac{1}{2\pi}}\sqrt{\frac{k_{eff}}{m_{eff}}} \approx 1.03\sqrt{\frac{E}{\rho}}\frac{h}{L^2}$$

where $k_{eff}$ is the effective stiffness of the resonator/top electrode material, $m_{eff}$ is the effective mass of the resonator/top electrode material (e.g., copper), E is Young's Modulus and $\rho$ is the density of the resonator/top electrode material. Thus, as the capacitance, C(t), changes with flexure of the resonator/top electrode structure, the voltage, $V_{in}(t)$, applied to the resonator/top electrode structure results in a proportional change in output current, $I_o(t)$.

Output current $I_o(t)$ from the structure 399 comprises a current that corresponds to a change in capacitance when the resonator vibrates at one of its natural frequencies. The change in the frequency of the output current capacitance corresponds to ultrasonic energy reflected from a tissue onto membrane/top electrode 373.

In one embodiment, the top electrode 373 may be connected in a positive feedback topology with a transimpedance amplifier that can be formed on a substrate (e.g., a silicon substrate on which the sensor is formed or another substrate coupled to the sensor) to provide an oscillator. The output of the oscillator is a signal with a frequency that is dependent on the sensed ultrasound energy from the tissue of the user and the frequency is counted with a simple counter circuit that can also be implemented on the silicon.

Sensor 399 may be formed at various critical dimensions (CD) unsuitable for prior technologies using, for example, aluminum which is limited to relatively older technologies that do not apply to deep submicron semiconductor manufacturing technologies. Sensor 399 may be included in small form factors with CDs of 22 nm, 14 nm, 10 nm, 7 nm, and the like.

In one embodiment the sensor 399 takes advantage of the low deposition (either sputtering or electroplating) temperature of copper to pattern a copper resonator structure on a flexible polymer substrate. Conventional technologies using, for example, aluminum (due to high flow temperature for aluminum) would not be compatible with polymer 310. The same is true for conventional technologies using, for example, amorphous silicon and/or low temperature oxide—both of which may require processing temperatures unsuitable for polymer 310. Using a polymer flexible substrate may enable a very flexible package that can be mechanically and electrically connected to any point in a platform, which provides flexibility of deployment. The sensor may be coupled to a printed circuit board or other substrate via wires and/or connectors (e.g., ZIF connector), which may allow the sensor to be positioned anywhere within the platform.

However, in other embodiments layers 300, 305, 310 may be substituted for with a substrate, such as a silicon substrate having a front end with device logic to perform the operations of, for example, microcontroller 194.

Various embodiments include a semiconductor substrate. Such a substrate may be a bulk semiconductive material that is part of a wafer. In an embodiment, the semiconductive substrate is a bulk semiconductive material as part of a chip that has been singulated from a wafer. In an embodiment, the semiconductive substrate is a semiconductive material that is formed above an insulator such as a semiconductor on insulator (SOI) substrate. In an embodiment, the semiconductive substrate is a prominent structure such as a fin that extends above a bulk semiconductive material.

Figure 4:
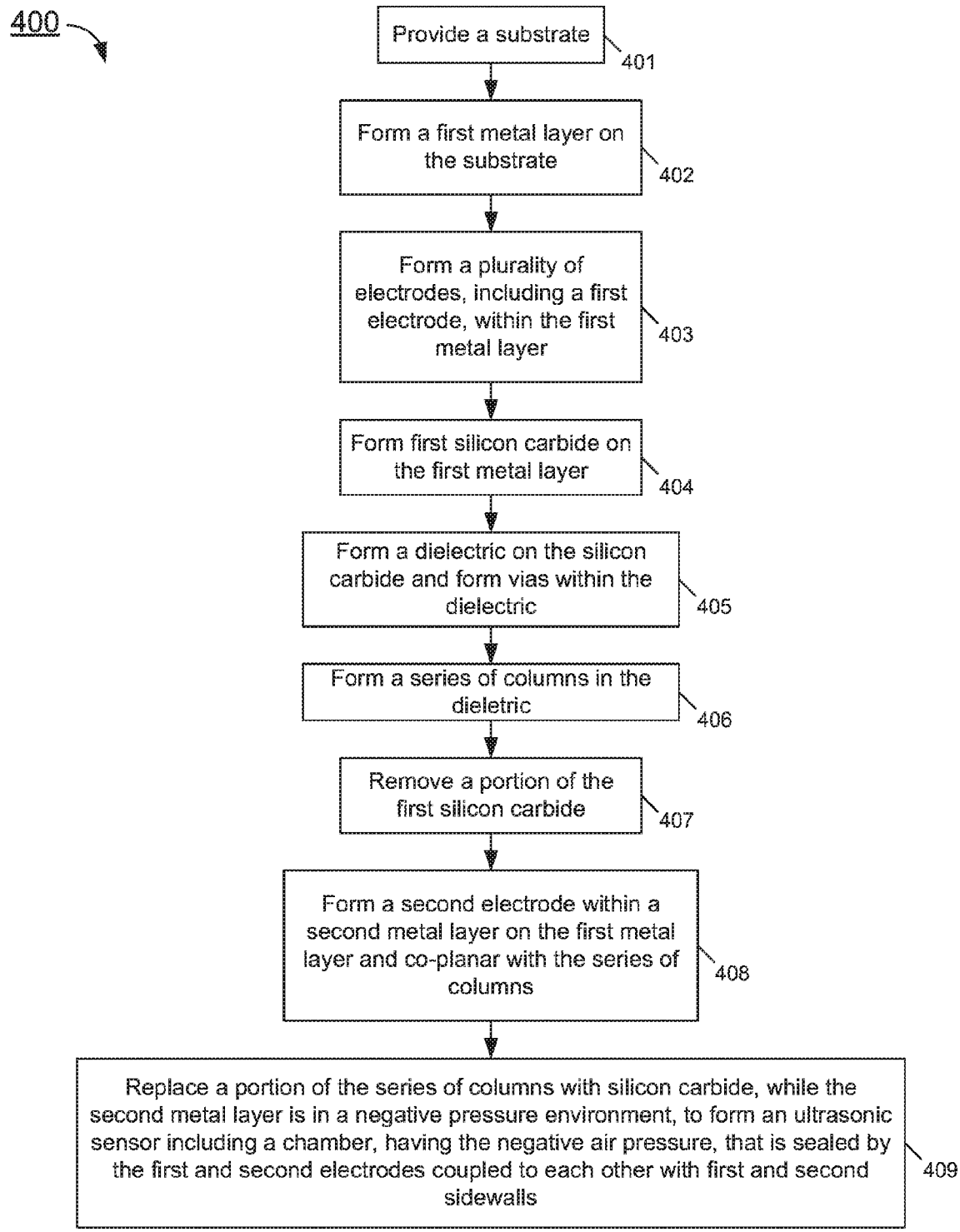
FIG. 4 includes a process in an embodiment.

FIG. 4 includes a process 400 in an embodiment. The method includes providing a substrate (block 401); forming a first metal layer on the substrate (block 402); forming a plurality of electrodes, including a first electrode, within the first metal layer (block 403); forming first silicon carbide on the first metal layer (block 404); forming a dielectric on the silicon carbide and forming vias within the dielectric (block 405); forming a series of columns in the dielectric (block 406); removing a portion of the first silicon carbide (block 407); forming a second electrode within a second metal layer on the first metal layer and co-planar with the series of columns (block 408); and replacing a portion of the series of columns with silicon carbide, while the second metal layer is in a negative pressure environment, to form an ultrasonic sensor including a chamber, having the negative air pressure, that is sealed by the first and second electrodes coupled to each other with first and second sidewalls (block 409).

Figure 5:
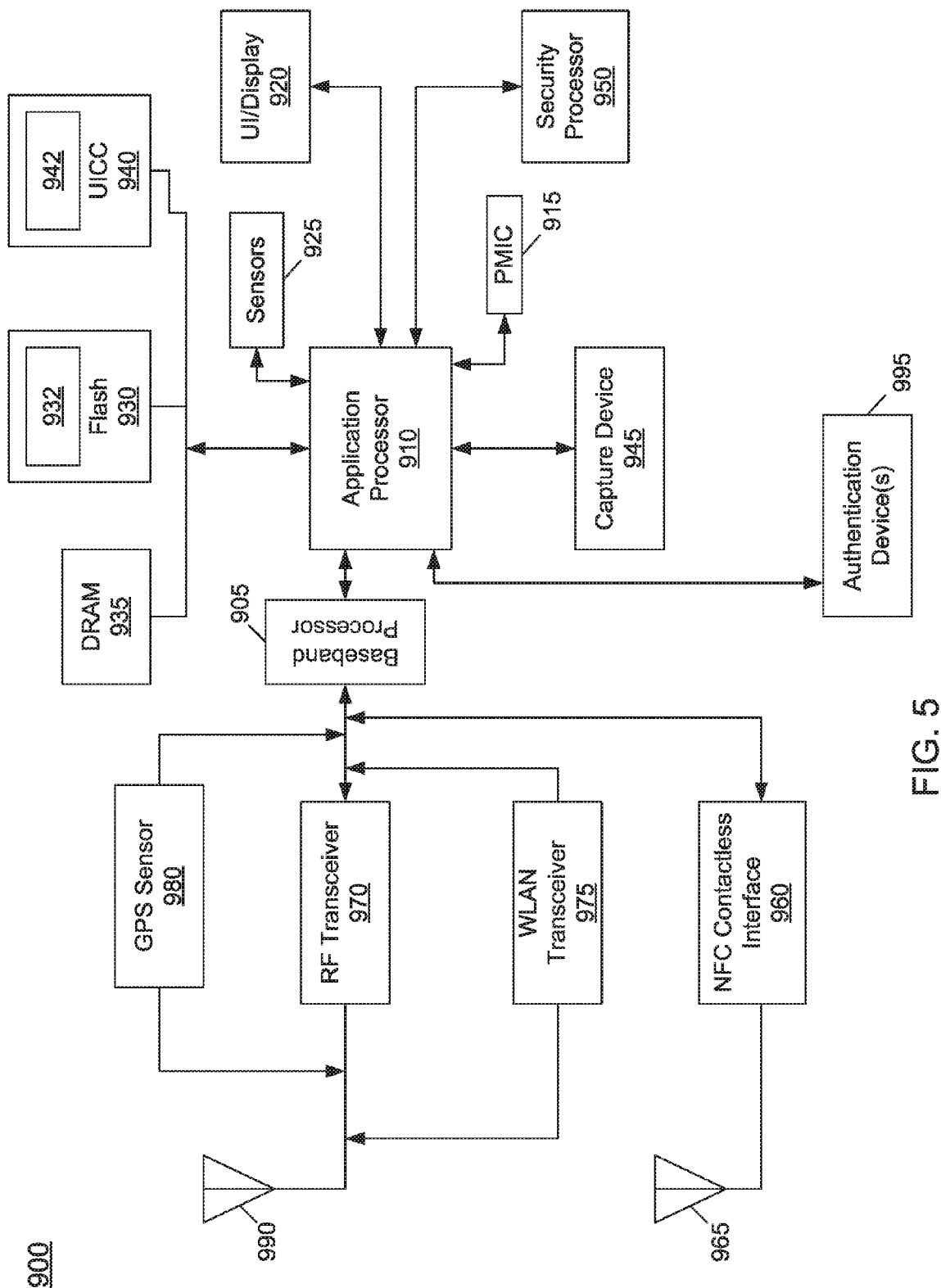
FIGS. 5 and 6 include systems for use in varying embodiments.

Referring now to FIG. 5, shown is a block diagram of an example system with which embodiments can be used. As seen, system 900 may be a smartphone or other wireless communicator or any other IoT device. A baseband processor 905 is configured to perform various signal processing with regard to communication signals to be transmitted from or received by the system. In turn, baseband processor 905 is coupled to an application processor 910, which may be a main CPU of the system to execute an OS and other system software, in addition to user applications such as many well-known social media and multimedia apps. Application processor 910 may further be configured to perform a variety of other computing operations for the device.

In turn, application processor 910 can couple to a user interface/display 920 (e.g., touch screen display). In addition, application processor 910 may couple to a memory system including a non-volatile memory, namely a flash memory 930 and a system memory, namely a DRAM 935. In some embodiments, flash memory 930 may include a secure portion 932 in which secrets and other sensitive information may be stored. As further seen, application processor 910 also couples to a capture device 945 such as one or more image capture devices that can record video and/or still images.

A universal integrated circuit card (UICC) 940 comprises a subscriber identity module, which in some embodiments includes a secure storage 942 to store secure user information. System 900 may further include a security processor 950 (e.g., Trusted Platform Module (TPM)) that may couple to application processor 910. A plurality of sensors 925, including one or more multi-axis accelerometers may couple to application processor 910 to enable input of a variety of sensed information such as motion and other environmental information. In addition, one or more authentication devices 995 may be used to receive, for example, user biometric input for use in authentication operations.

As further illustrated, a near field communication (NFC) contactless interface 960 is provided that communicates in a NFC near field via an NFC antenna 965. While separate antennae are shown, understand that in some implementations one antenna or a different set of antennae may be provided to enable various wireless functionalities.

A power management integrated circuit (PMIC) 915 couples to application processor 910 to perform platform level power management. To this end, PMIC 915 may issue power management requests to application processor 910 to enter certain low power states as desired. Furthermore, based on platform constraints, PMIC 915 may also control the power level of other components of system 900.

To enable communications to be transmitted and received such as in one or more IoT networks, various circuitry may be coupled between baseband processor 905 and an antenna 990. Specifically, a radio frequency (RF) transceiver 970 and a wireless local area network (WLAN) transceiver 975 may be present. In general, RF transceiver 970 may be used to receive and transmit wireless data and calls according to a given wireless communication protocol such as 3G or 4G wireless communication protocol such as in accordance with a code division multiple access (CDMA), global system for mobile communication (GSM), long term evolution (LTE) or other protocol. In addition a GPS sensor 980 may be present, with location information being provided to security processor 950 for use as described herein when context information is to be used in a pairing process. Other wireless communications such as receipt or transmission of radio signals (e.g., AM/FM) and other signals may also be provided. In addition, via WLAN transceiver 975, local wireless communications, such as according to a Bluetooth™ or IEEE 802.11 standard can also be realized.

Figure 6:
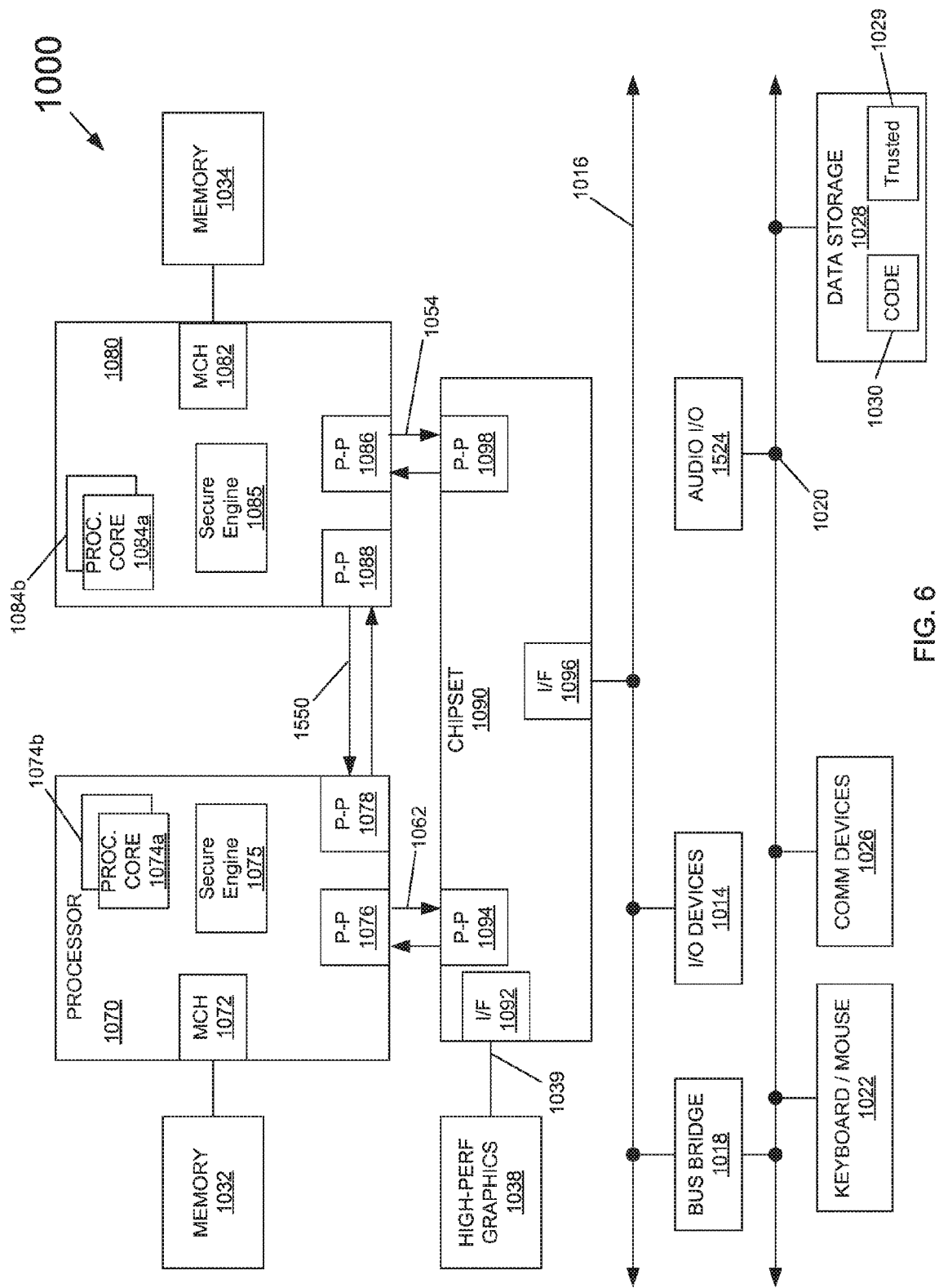

Referring now to FIG. 6, shown is a block diagram of a system in accordance with another embodiment of the present invention. Multiprocessor system 1000 is a point-to-point interconnect system such as a server system, and includes a first processor 1070 and a second processor 1080 coupled via a point-to-point interconnect 1050. Each of processors 1070 and 1080 may be multicore processors such as SoCs, including first and second processor cores (i.e., processor cores 1074a and 1074b and processor cores 1084a and 1084b), although potentially many more cores may be present in the processors. In addition, processors 1070 and 1080 each may include a secure engine 1075 and 1085 to perform security operations such as attestations, IoT network onboarding or so forth.

First processor 1070 further includes a memory controller hub (MCH) 1072 and point-to-point (P-P) interfaces 1076 and 1078. Similarly, second processor 1080 includes a MCH 1082 and P-P interfaces 1086 and 1088. MCH's 1072 and 1082 couple the processors to respective memories, namely a memory 1032 and a memory 1034, which may be portions of main memory (e.g., a DRAM) locally attached to the respective processors. First processor 1070 and second processor 1080 may be coupled to a chipset 1090 via P-P interconnects 1052 and 1054, respectively. Chipset 1090 includes P-P interfaces 1094 and 1098.

Furthermore, chipset 1090 includes an interface 1092 to couple chipset 1090 with a high performance graphics engine 1038, by a P-P interconnect 1039. In turn, chipset 1090 may be coupled to a first bus 1016 via an interface 1096. Various input/output (I/O) devices 1014 may be coupled to first bus 1016, along with a bus bridge 1018 which couples first bus 1016 to a second bus 1020. Various devices may be coupled to second bus 1020 including, for example, a keyboard/mouse 1022, communication devices 1026 and a data storage unit 1028 such as a non-volatile storage or other mass storage device. As seen, data storage unit 1028 may include code 1030, in one embodiment. As further seen, data storage unit 1028 also includes a trusted storage 1029 to store sensitive information to be protected. Further, an audio I/O 1024 may be coupled to second bus 1020.

An embodiment includes the sensor of FIG. 3(j) in the system of FIG. 1 within the platform of FIG. 5. For example, a mobile computing node (e.g., Smartphone or IoT node) may include the sensor as a login device for authentication purposes. The processor (also referred to as controller 194) of FIG. 1 may actually compare the sensed information from sensor 196 (sensor 925 in FIG. 5) to a template stored locally (e.g., within memory 932) and then complete authentication of the user so the user may access privileged areas (e.g., security processor 950). However, in other embodiments the system of FIG. 5 may take a sensed value from sensor 925, encrypt that value, and then communicate the value to a remote node, such as a server system shown in FIG. 6. The server system 1000 may compare the communicated value to a template and perform authentication of the user.

Embodiments may be used in many different types of systems. For example, in one embodiment a communication device can be arranged to perform the various methods and techniques described herein. Of course, the scope of the present invention is not limited to a communication device, and instead other embodiments can be directed to other types of apparatus for processing instructions, or one or more machine readable media including instructions that in response to being executed on a computing device, cause the device to carry out one or more of the methods and techniques described herein.

Embodiments may be implemented in code and may be stored on a non-transitory storage medium having stored thereon instructions which can be used to program a system to perform the instructions. Embodiments also may be implemented in data and may be stored on a non-transitory storage medium, which if used by at least one machine, causes the at least one machine to fabricate at least one integrated circuit to perform one or more operations. The storage medium may include, but is not limited to, any type of disk including floppy disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

The following examples pertain to further embodiments.

Example 1 a backend material stack including a first metal layer between a substrate and a second metal layer with each of the first and second metal layers including a dielectric material; a ultrasonic sensor including a chamber, having a negative air pressure, that is sealed at least in part by first and second electrodes coupled to each other with first and second sidewalls; an interconnect, not included in the sensor, in the second metal layer; wherein (a) a first vertical axis intersects the substrate, the chamber, and the first and second electrodes, (b) a second vertical axis intersects the interconnect and the substrate, (c) a first horizontal axis intersects the chamber, the interconnect, and the first and second sidewalls, (d) the first and second electrodes and the first and second sidewalls each include copper; and (e) the first electrode and the first and second sidewalls are included in the second metal layer.

For example, in FIG. 3(j) layer 352 includes a first metal layer and layer 351 includes a second metal layer. An interconnect 353, which is not part of the sensor, is also in the metal layer 351. Vertical axis 354 intersects the substrate, the chamber, and the first and second electrodes (394, 373). Vertical axis 356 intersects the interconnect and the substrate. Horizontal axis 357 intersects the chamber, the interconnect 353, and the first and second sidewalls 371, 372.

The negative air pressure is taken relative to surroundings of the system. In an embodiment the negative air pressure constitutes a vacuum relative to atmospheric pressure at sea level. Also, the chamber is sealed at least in part by first and second electrodes coupled to each other with first and second sidewalls. For example, a dielectric material may also be needed to seal the chamber.

Such an embodiment provides a low-cost based ultrasound imaging technology that will fit into small form factors (e.g., phone or IoT wearable devices) to generate on-the-fly images for biometric encryption.

In an embodiment, the first and second metal layers may be any of M0-M11 in FIG. 2.

In example 2 the subject matter of the Example 1 can optionally include wherein the first electrode includes a first portion including copper and a second portion including silicon carbide.

In example 3 the subject matter of the Examples 1-2 can optionally include wherein a second horizontal axis intersects the first and second portions and the interconnect.

For example, axis 358 intersects portions 375 and 373.

In example 4 the subject matter of the Examples 1-3 can optionally include wherein the copper directly contacts the silicon carbide.

In example 5 the subject matter of the Examples 1-4 can optionally include wherein the first electrode includes a plurality of perforations that include the silicon carbide.

For example, the perforations 374 include silicon carbide portions 375.

In example 6 the subject matter of Examples 1-5 can optionally include a controller to couple to a current source; at least one non-transitory storage medium having instructions stored thereon for causing the controller to: apply first current at a first frequency to the first electrode; and after applying the first current, apply bias current to the first electrode while: (a) the first electrode is subjected to ultrasound energy, and (b) generating an output signal corresponding to a frequency of the ultrasound energy.

The at least one non-transitory storage medium may include memory, hardware logic, and/or firmware logic. Thus, in an embodiment bias current is overlaid with the first current to induce ultrasonic energy into a tissue. Once energy is reflected back to the first electrode from the tissue the first electrode, while bias, will resonate at a frequency indicative of a biometric (e.g., arrangement of blood vessels in a finger, a fingerprint, and the like).

In example 7 the subject matter of the Examples 1-6 can optionally include wherein the output signal is specific to a biometric.

In example 8 the subject matter of the Examples 1-7 can optionally include wherein the biometric is at least one of a fingerprint, a vascular pattern, and blood flow.

In example 9 the subject matter of the Examples 1-8 can optionally include wherein the biometric is at least one of a fingerprint and a vascular pattern.

In example 10 the subject matter of the Examples 1-9 can optionally include a system on a chip (SoC) that includes the controller and the sensor.

In example 11 the subject matter of the Examples 1-10 can optionally include wherein the output signal comprises a current that corresponds to a change in capacitance when the first electrode vibrates at one of its natural frequencies, the change in the frequency of the output current capacitance corresponding to a biometric.

Via thickness (see via that forms sidewall) defines the capacitive gap of the chamber.

In example 12 the subject matter of the Examples 1-11 can optionally include a controller to couple to a current source; at least one non-transitory storage medium having instructions stored thereon for causing the controller to: apply first current at a first frequency to the first electrode; and after applying the first current, apply first bias current to the first electrode while: (a) the first electrode is subjected to first ultrasound energy, and (b) generating a first output signal corresponding to a first frequency of the ultrasound energy that corresponds to a first biometric of a user; apply second current at a second frequency to the first electrode; and after applying the second current, apply second bias current to the first electrode while: (a) the first electrode is subjected to second ultrasound energy, and (b) generating a second output signal corresponding to a second frequency of the ultrasound energy that corresponds to a second biometric of the user.

For example, the first frequency may be target towards surface tissue for a fingerprint and the second frequency may be targeted more deeply in the tissue to determine a vascular pattern.

In example 13 the subject matter of the Examples 1-12 can optionally include wherein the sensor is a capacitive micromachined ultrasonic transducer (CMUT).

In example 14 the subject matter of the Examples 1-13 can optionally include wherein the substrate includes a flexible polymer.

The flexible polymer may or may not include or support transistors that can be manufactured on the polymer substrate. For example, the flexible polymer substrate may have organic field effect transistors (OFETs) (e.g., pentacene OFETs) manufactured on the substrate. This would be followed by depositing the interconnect layers to electrically connect these transistors. The interconnects can be of one, two, or more metal layers. While FIG. 3(*j*) may show layer 310 contacting ILD 315 this is not to say that other embodiments do not include other layers between layer 310 and ILD 315.

In example 15 the subject matter of the Examples 1-14 can optionally include wherein the polymer includes at least one of polyethylene terephthalate (PET) and poly(methylmethacrylate) (PMMA).

In example 16 the subject matter of the Examples 1-15 can optionally include, wherein the first sidewall is a damascene interconnect.

The damascene interconnect may include single or double damascene interconnects.

In example 17 the subject matter of the Examples 1-16 can optionally include wherein the substrate includes a plurality of transistors communicatively coupled to the first sidewall.

In example 18 the subject matter of the Examples 1-17 can optionally include wherein the plurality of transistors include positive carrier and negative carrier type transistors and the substrate is a monolithic wafer.

For example, the transistors may be a CMOS technology.

In example 19 the subject matter of the Examples 1-18 can optionally include wherein the substrate is included in a frontend of the stack and the sensor is included in the backend of the stack.

In example 20 the subject matter of the Examples 1-19 can optionally include an additional interconnect included in the first metal layer, wherein a third vertical axis intersects the first sidewall and the additional interconnect.

For example, axis 359 intersects the first sidewall 371 and the interconnect 392.

Example 21 includes a method comprising: providing a substrate; forming a first metal layer on the substrate; forming a plurality of electrodes, including a first electrode, within the first metal layer; forming first silicon carbide on the first metal layer; forming a dielectric on the silicon carbide and forming vias within the dielectric; forming a series of columns in the dielectric; removing a portion of the first silicon carbide; forming a second electrode within a second metal layer on the first metal layer and co-planar with the series of columns; replacing a portion of the series of columns with silicon carbide, while the second metal layer is in a negative pressure environment, to form an ultrasonic sensor including a chamber, having the negative air pressure, that is sealed by the first and second electrodes coupled to each other with first and second sidewalls; wherein (a) the first and second electrodes and the first and second sidewalls each include copper, and (b) the first electrode and the first and second sidewalls are included in the second metal layer.

In example 22 the subject matter of the Example 21 can optionally include wherein (a) a first vertical axis intersects the substrate, the chamber, and the first and second electrodes, (b) a second vertical axis intersects an interconnect and the substrate, and (c) a first horizontal axis intersects the chamber, the interconnect, and the first and second sidewalls.

Example 23 includes a system-on-chip (SoC) comprising: a first metal layer between a substrate and a second metal layer; an ultrasound sensor including a chamber, having a negative air pressure, sealed by first and second electrodes coupled to each other with first and second sidewalls; an interconnect, not included in the sensor, in the second metal layer; and control logic, including transistors in the substrate, to apply (a) first current at a first frequency to the first electrode; and (b) bias current to the first electrode while generating an output signal corresponding to a biometric of a user; wherein: (c) a first vertical axis intersects the substrate, the chamber, and the first and second electrodes, (d) a second vertical axis intersects the interconnect and the substrate, (e) a first horizontal axis intersects the chamber, the interconnect, and the first and second sidewalls, (f) the first and second electrodes and the first and second sidewalls each include copper, and (g) the first electrode and the first and second sidewalls are included in the second metal layer.

In example 24 the subject matter of the Example 23 can optionally include wherein: the first electrode includes a first portion including copper and a second portion including silicon carbide; and a second horizontal axis intersects the first and second portions and the interconnect.

In example 25 the subject matter of Examples 23-24 can optionally include an additional ultrasound sensor including an additional chamber, having a negative air pressure, sealed at least in part by additional first and second electrodes coupled to each other with additional first and second sidewalls; additional control logic to apply (a) additional current at an additional frequency to the additional first electrode; and (b) additional bias current to the additional first electrode while generating an additional output signal corresponding to an additional biometric of the user; wherein the first frequency is unequal to the additional frequency; wherein the first electrode has a first surface area corresponding to the first frequency and the additional first electrode has an additional surface area, unequal to the first surface area, corresponding to the additional frequency.

For example, a system may include an array of sensors. The sensors may have resonating electrodes that resonate at different frequencies based on their different sizes. For example, the above "first electrode" may have a first area in the horizontal plane (X*Y) and the "additional first electrode" may have a bigger area in the same horizontal plane. The same bias and AC currents may be applied to each electrode but doing so would result in different frequencies being communicated to a user's tissue based on the differing sizes of the electrodes. One frequency may target the tissue surface (e.g., finger print) while another focuses more deeply on vasculature. Differing frequencies may also be generated within each sensor by varying the AC overlaid on the bias. Varying electrode sizes just adds to the potential choices of frequencies to communicate to the tissue. Thus, the system may target different tissue depths based on different AC frequency and/or different electrode size. One array may have two subarrays, with each having differently sized electrodes and with each subarray being driven at a different AC.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a device side (or active surface) of a substrate or integrated circuit is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. An ultrasonic sensor system comprising:
    a backend material stack including a first metal layer between a substrate and a second metal layer with each of the first and second metal layers including a dielectric material;
    a ultrasonic sensor including a chamber, having a negative air pressure, that is sealed at least in part by first and second electrodes coupled to each other with first and second sidewalls;
    an interconnect, not included in the sensor, in the second metal layer;
    wherein (a) a first vertical axis intersects the substrate, the chamber, and the first and second electrodes, (b) a second vertical axis intersects the interconnect and the substrate, (c) a first horizontal axis intersects the chamber, the interconnect, and the first and second sidewalls, (d) the first and second electrodes and the first and second sidewalls each include copper; and (e) the first electrode and the first and second sidewalls are included in the second metal layer.

2. The system of claim 1, wherein the first electrode includes a first portion including copper and a second portion including silicon carbide.

3. The system of claim 2, wherein a second horizontal axis intersects the first and second portions and the interconnect.

4. The system of claim 2, wherein the copper directly contacts the silicon carbide.

5. The system of claim 2, wherein:
    the first electrode includes a plurality of perforations that include the silicon carbide; and
    the second electrode is in the first metal layer.

6. The system of claim 1 comprising:
a controller to couple to a current source; and
at least one non-transitory storage medium having instructions stored thereon for causing the controller to:
apply first current at a first frequency to the first electrode; and
after applying the first current, apply bias current to the first electrode while: (a) the first electrode is subjected to ultrasound energy, and (b) generating an output signal corresponding to a frequency of the ultrasound energy.

7. The system of claim 6, wherein the output signal is specific to a biometric.

8. The system of claim 7, wherein the biometric is at least one of a fingerprint, a vascular pattern, and blood flow.

9. The system of claim 7, wherein the biometric is at least one of a fingerprint and a vascular pattern.

10. The system of claim 7 comprising a system on a chip (SoC) that includes the controller and the sensor.

11. The system of claim 6, wherein the output signal comprises a current that corresponds to a change in capacitance when the first electrode vibrates at one of its natural frequencies.

12. The system of claim 1 comprising:
a controller to couple to a current source;
at least one non-transitory storage medium having instructions stored thereon for causing the controller to:
apply first current at a first frequency to the first electrode; and
after applying the first current, apply first bias current to the first electrode while: (a) the first electrode is subjected to first ultrasound energy, and (b) generating a first output signal corresponding to a first frequency of the ultrasound energy that corresponds to a first biometric of a user;
apply second current at a second frequency to the first electrode; and
after applying the second current, apply second bias current to the first electrode while: (a) the first electrode is subjected to second ultrasound energy, and (b) generating a second output signal corresponding to a second frequency of the ultrasound energy that corresponds to a second biometric of the user.

13. The system of claim 1, wherein the sensor is a capacitive micromachined ultrasonic transducer (CMUT).

14. The system of claim 13, wherein the substrate includes a flexible polymer.

15. The system of claim 14, wherein the polymer includes at least one of polyethylene terephthalate (PET) and poly(methyl-methacrylate) (PMMA).

16. The system of claim 13, wherein the first sidewall is a damascene interconnect.

17. The system of claim 16, wherein the substrate includes a plurality of transistors communicatively coupled to the first sidewall.

18. The system of claim 17, wherein the plurality of transistors include positive carrier and negative carrier type transistors and the substrate is a monolithic wafer.

19. The system of claim 17, wherein the substrate is included in a frontend of the stack and the sensor is included in the backend of the stack.

20. The system of claim 13 comprising an additional interconnect included in the first metal layer, wherein a third vertical axis intersects the first sidewall and the additional interconnect.

21. A method comprising:
providing a substrate;
forming a first metal layer on the substrate;
forming a plurality of electrodes, including a first electrode, within the first metal layer;
forming first silicon carbide on the first metal layer;
forming a dielectric on the silicon carbide and forming vias within the dielectric;
forming a series of columns in the dielectric;
removing a portion of the first silicon carbide;
forming a second electrode within a second metal layer on the first metal layer and co-planar with the series of columns;
replacing a portion of the series of columns with silicon carbide, while the second metal layer is in a negative pressure environment, to form an ultrasonic sensor including a chamber, having the negative air pressure, that is sealed at least in part by the first and second electrodes coupled to each other with first and second sidewalls;
wherein (a) the first and second electrodes and the first and second sidewalls each include copper, and (b) the first electrode and the first and second sidewalls are included in the second metal layer.

22. The method of claim 21, wherein (a) a first vertical axis intersects the substrate, the chamber, and the first and second electrodes, (b) a second vertical axis intersects an interconnect and the substrate, and (c) a first horizontal axis intersects the chamber, the interconnect, and the first and second sidewalls.

23. A system comprising:
a system-on-chip (SoC) comprising:
a first metal layer between a substrate and a second metal layer;
an ultrasound sensor including a chamber, having a negative air pressure, sealed at least in part by first and second electrodes coupled to each other with first and second sidewalls;
an interconnect, not included in the sensor, in the second metal layer; and
control logic, including transistors in the substrate, to apply (a) first current at a first frequency to the first electrode; and (b) bias current to the first electrode while generating an output signal corresponding to a biometric of a user;
wherein: (c) a first vertical axis intersects the substrate, the chamber, and the first and second electrodes, (d) a second vertical axis intersects the interconnect and the substrate, (e) a first horizontal axis intersects the chamber, the interconnect, and the first and second sidewalls, (f) the first and second electrodes and the first and second sidewalls each include copper, and (g) the first electrode and the first and second sidewalls are included in the second metal layer.

24. The system of claim 23, wherein:
the first electrode includes a first portion including copper and a second portion including silicon carbide; and
a second horizontal axis intersects the first and second portions and the interconnect.

25. The system of claim 23 comprising:
an additional ultrasound sensor including an additional chamber, having a negative air pressure, sealed at least in part by additional first and second electrodes coupled to each other with additional first and second sidewalls;
additional control logic to apply (a) additional current at an additional frequency to the additional first electrode; and (b) additional bias current to the additional first electrode while generating an additional output signal corresponding to an additional biometric of the user;

wherein the first frequency is unequal to the additional frequency;

wherein the first electrode has a first surface area corresponding to the first frequency and the additional first electrode has an additional surface area, unequal to the first surface area, corresponding to the additional frequency.

* * * * *